United States Patent [19]

Kreft, III et al.

[11] Patent Number: 4,661,596
[45] Date of Patent: Apr. 28, 1987

[54] QUINOLINYL (OR PYRIDINYL) METHOXY SUBSTITUTED NAPHTHALENE COMPOUNDS AS ANTIALLERGIC AGENTS

[75] Inventors: Anthony F. Kreft, III, Devon; John H. Musser, Malvern; Thomas W. Pattison; John P. Yardley, both of King of Prussia, all of Pa.

[73] Assignee: American Home Products Corporation, New York, N.Y.

[21] Appl. No.: 784,141

[22] Filed: Oct. 3, 1985

Related U.S. Application Data

[63] Continuation-in-part of Ser. No. 703,788, Feb. 21, 1985, abandoned.

[51] Int. Cl.$^4$ ................. C07D 215/00; C07D 213/30
[52] U.S. Cl. .................... 546/152; 544/336; 544/353; 546/339; 548/179; 548/203; 548/217; 548/235; 548/305; 548/342
[58] Field of Search ............... 544/336, 353; 546/152, 546/339; 514/249, 255, 277, 311

[56] References Cited

U.S. PATENT DOCUMENTS

Re. 31,624  7/1984  Dewhirst ..................... 546/339
4,563,526  1/1986  Dewhirst ..................... 546/339

FOREIGN PATENT DOCUMENTS 45-12319  5/1970  Japan ........................ 546/339

OTHER PUBLICATIONS

Kurosu et al, Chem. Abst. 89-101973n.
Gordon et al, Abstract 266 in Prostaglandins and Leukotrienes, 1984, George Washington Medical School, Washington, DC, May 8-11, 1984.

Primary Examiner—Donald G. Daus
Assistant Examiner—Cecilia Shen
Attorney, Agent, or Firm—George Tarnowski

[57] ABSTRACT

There are disclosed compounds of the formula

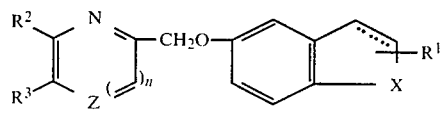

wherein
X is —CH$_2$CH$_2$—, —CH=CH—,

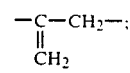

Z is CR or N, when n=1; or Z is O, S, or NR, when n=0;
R is hydrogen or loweralkyl;
n is 0 or 1;
R$^1$ is hydroxy, amino, loweralkyl sulfonamido, perfluoro loweralkyl sulfonamido or OR;
R$^2$ is hydrogen or loweralkyl;
R$^3$ is hydrogen or loweralkyl; or
R$^2$ and R$^3$ taken together form a benzene ring; and the dotted line represents an optional double bond;
and the pharmaceutically acceptable salts thereof, and their use in the treatment of leukotriene-mediated nasobronchial obstructive airpassageway conditions, such as allergic rhinitis, allergic bronchial asthma and the like.

10 Claims, No Drawings

QUINOLINYL (OR PYRIDINYL) METHOXY SUBSTITUTED NAPHTHALENE COMPOUNDS AS ANTIALLERGIC AGENTS

This is a continuation-in-part of U.S. Ser. No. 703,788 filed Feb. 21, 1985, now abandoned.

This invention relates to novel naphthalene compounds possessing lipoxygenase inhibitory and slow-reacting substance of anaphylaxis (SRS-A) antagonist activity which are useful as anti-inflammatory and anti-allergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of these AA metabolites has been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126(1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217(1982).

The biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or antagonizing their effects. Thus, compounds which inhibit the biological effects of the leukotrienes and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula wherein

X is $-CH_2-CH_2-$, $-CH=CH-$ or $$-\underset{\underset{CH_2}{\|}}{C}-CH_2-$$

Z is CR or N, when n=1; or Z is O, S, or NR when n=0;

R is hydrogen or loweralkyl;

n is 0 or 1;

$R^1$ is hydroxy, amino, loweralkyl sulfonamido, perfluoro loweralkyl sulfonamido or OR;

$R^2$ is hydrogen or loweralkyl;

$R^3$ is hydrogen or loweralkyl; or $R^2$ and $R^3$ taken together form a benzene ring; and the dotted lines represent optional double bonds;

and the pharmaceutically acceptable salts thereof.

The term "loweralkyl" refers to moieties having 1–6 carbon atoms.

The compounds of the invention can be prepared in the following manner;

wherein Z, n, $R^1$, $R^2$ and $R^3$ are as defined hereinbefore and hal refers to a halo radical, for example, chloro or bromo. The reaction is carried out in an organic solvent, for instance, dimethylformamide, at reduced temperature under a nitrogen atmosphere. The naphthalene intermediate in the above reaction sequence can be employed in its alkali metal derivative form.

Compounds of the invention in which the naphthalene portion of the molecule have the formula:

can be prepared as described supra using a 7-hydroxytetralone, followed by reduction of the ketone to the alcohol form, for example:

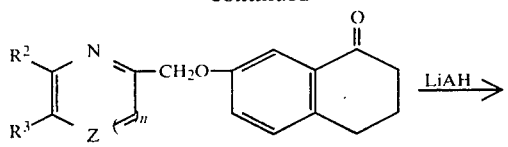

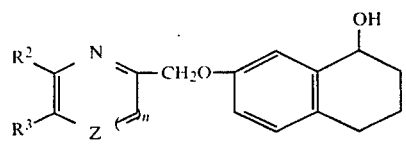

where Z, n, $R^1$, $R^2$, $R^3$ and hal are as defined hereinbefore. The reduction is carried out in an organic solvent, for example, tetrahydrofuran, under a nitrogen atmosphere.

Compounds in which the naphthalene portion of the molecule have the formula

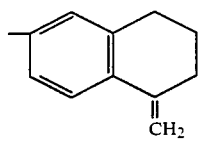

can be prepared as described supra using a 7-hydroxytetralone, followed by a Wittig reaction:

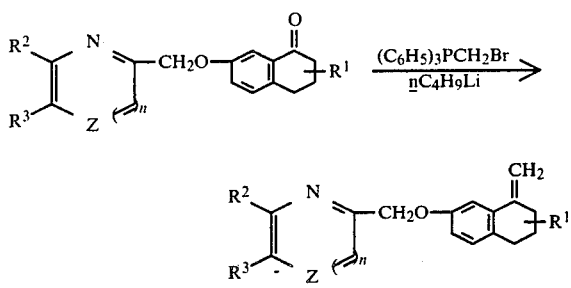

wherein Z, n, $R^1$, $R^2$, and $R^3$ are as defined hereinbefore. The reaction is carried out in an organic solvent for example, tetrahydrofuran, under a nitrogen atmosphere.

Compounds in which $R^1$ is loweralkyl sulfonamido can be prepared by the procedures described hereinbefore, using an appropriate amino-2-naphthol, e.g. the sodio derivative thereof, as the starting intermediate, and in the final reaction step, reacting the resulting amine with a loweralkyl or perfluoro loweralkyl sulfonyl halide:

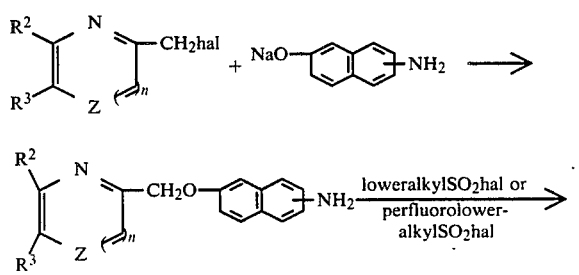

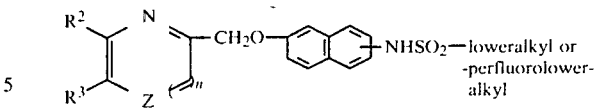

wherein Z, n, $R^2$, $R^3$ loweralkyl and hal are as defined hereinbefore.

The starting compounds in the above preparative sequences are commercially available or can be prepared by conventional methods known in the art.

The compounds of the invention are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic, oxalic and the like.

The compounds of the invention, by virtue of their ability to inhibit the activity of lipoxygenase enzyme and by their ability to antagonize the effects of $LTD_4$ and $LTC_4$, which are the major constituents of SRS-A, are useful for the inhibition of symptoms induced by these leukotrienes. Accordingly, the compounds are indicated in the prevention and treatment of those disease states in which $LTD_4$ and $LTC_4$ are causative factors, for example, allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE, and measure the in vivo activity of the compounds as lipoxygenase inhibitors and leukotriene antagonists of endogenous mediators of bronchospasm.

The following examples show the preparation and pharmacological testing of compounds within the invention.

EXAMPLE 1

1,2,3,4-Tetrahydro-7-(2-quinolinylmethoxy)-1-naphthalenol

A.

3,4-Dihydro-7-(2-quinolinylmethoxy)-1(2H)-naphthalenone

To a slurry of NaH (0.29 g, 12.25 mmol) in 25 mL dimethylformamide under nitrogen at 0° C. is added portionwise 7-hydroxy-1-tetralone (2.0 g, 12.33 mmol) over 5 minutes. After half an hour, 2-(chloromethyl)-quinoline (2.2 g, 12.43 mmol) is added in 10 mL dimethylformamide. The ice bath is removed and the reaction mixture is stirred overnight. The solvent is then removed in vacuo and the residue is partitioned between 1N sodium hydroxide and methylene chloride. The organic layer is separated, dried over magnesium sulfate, evaporated down to an oil, and chromatographed on silica gel. Elution with 9-1 methylene chloride/ethyl acetate gives 2.0 g(54%). This material is recrystallized from acetonitrile to afford 1.3 g (35%) of yellow crystals, m.p. 98.5°–101.5° C.

Analysis for: $C_{20}H_{17}NO_2$:
Calculated: C, 79.18; H, 5.65; N, 4.62.
Found: C, 79.09; H, 5.65; N, 4.70.

B.

1,2,3,4-Tetrahydro-7-(2-quinolinylmethoxy)-1-naphthalenol

To a solution of 0.62 g (16.33 mmol) lithium aluminum hydride in 80 mL tetrahydrofuran under nitrogen at 0° C. is added dropwise with stirring a solution of 5.0 g (16.48 mmol) of 3,4-dihydro-7-(2-quinolinylmethoxy)-1(2H)-naphthalenone over 1 minute. The ice bath is removed and after 1 hour the reaction is worked up according to Micovic and Mihailovic[1]. The crude product is recrystallized from ethylacetate/hexane and affords 3.1 g (62%) of white crystals, m.p. 113°–115° C.

Analysis for: $C_{20}H_{19}NO_2$:
Calculated: C, 78.66; H, 6.27; N, 4.59.
Found: C, 79.15; H, 6.23; N, 4.81.

[1] Micovic and Mihailovic, *J. Org. Chem.*, 18, 1190 (1953).

EXAMPLE 2

7-(2-quinolinylmethoxy)-2-naphthalenol

The title compound is obtained by using the procedure of Example 1 for preparation of the starting material, but using 2,7-naphthalenediol. The workup is modified as follows: after removal of the dimethylformamide in vacuo, water is added to the residue and the insolubles are filtered off and dried, recrystallized from acetonitrile, the crystals are treated with 9:1 hexane/ethyl acetate and the insoluble portion is recrystallized from acetonitrile to afford white crystals, m.p. 218°–220° C. HPLC analysis (μPorasil, 9:1 methylene chloride/ethyl acetate) reveals a purity of 98%.

Analysis for: $C_{20}H_{15}NO_2$:
Calculated: C, 79.71; H, 5.02; N, 4.64.
Found: C, 79.94; H, 4.91; N, 4.83.

EXAMPLE 3

2-[[(7-methoxy-2-naphthalenyl)oxy]methyl]quinoline

The title compound is obtained by using the procedure of Example 1 for preparation of the starting material utilizing methyl iodide and 7-(2-quinolinylmethoxy)-2-naphthalenol. The workup is modified as follows: after removal of the dimethylformamide in vacuo, water is added to the residue and the insolubles are filtered off and dried and chromatographed on silica gel (eluant: methylene chloride). Recrystallization from methanol affords white crystals, m.p. 113°–114.5° C.

Analysis for: $C_{21}H_{17}NO_2$:
Calculated: C, 79.98; H, 5.44; N, 4.44.
Found: C, 80.47; H, 5.45; N, 4.49.

EXAMPLE 4

7-(2-benzothiazolylmethoxy)-2-naphthalenol

The title compound is obtained by using the procedure of Example 1 for preparation of the starting material utilizing 2-(chloromethyl)-benzothiazole and 2,7-naphthalenediol. The workup used is that of Example 2 up to the first recrystallization where the solvent is changed to toluene. Yellow crystals are obtained, m.p. 205°–207° C.

Analysis for: $C_{18}H_{13}NO_2S$:
Calculated: C, 70.33; H, 4.26; N, 4.56.
Found: C, 70.72; H, 4.30; N, 4.79.

EXAMPLE 5

7-(2-pyridinylmethoxy)-2-naphthalenol

The title compound is obtained by using the procedure of Example 4 but using methanol as the recrystallization solvent and using 2-(chloromethyl)pyridine and 2,7-naphthalenediol. Brown crystals are obtained, m.p. 190°–193° C.

Analysis for: $C_{16}H_{13}NO_2$:
Calculated: C, 76.48; H, 5.21; N, 5.58.
Found: C, 76.49; H, 5.25; N, 5.57.

EXAMPLE 6

7-(2-quinolinylmethoxy)-1-naphthalenamine

The title compound is obtained by using the procedure of Example 4 using 2-(chloromethyl)quinoline and 1-amino-7-hydroxy-naphthalene. Brown crystals are obtained, m.p. 148° C. (dec.).

Analysis for: $C_{20}H_{16}N_2O$:
Calculated: C, 79.97; H, 5.37; N, 9.16.
Found: C, 80.34; H, 5.38; N, 9.45.

EXAMPLE 7

7-(2-quinolinylmethoxy)-2-naphthalenamine

To a suspension of 40.0 g 7-amino-2-naphthol hydrochloride (205 mmol) in 250 mL methanol under nitrogen is added 451 mL of 0.91N sodium methoxide (410 mmol) in methanol. After 1 hour of stirring, the solvent is removed and the residue is taken up in 500 mL dimethylformamide and cooled to 10° C. under nitrogen. A solution of 36.3 g 2-(chloromethyl)quinoline (205 mmol) in 200 mL dimethylformamide is added. After stirring overnight at ambient temperature, the reaction is stripped of solvent, water is added and the precipitate is filtered off, dried and recrystallized from toluene to afford 31.1 g (62%) of white crystals, which is further purified by filtration through Florisil. Recrystallization from toluene affords white crystals, m.p. 164.5°–166.0° C.

Analysis for: $C_{20}H_{16}N_2O$:
Calculated: C, 79.97; H, 5.37; N, 9.33.
Found: C, 80.07; H, 5.33; N, 9.10.

EXAMPLE 8

N-[7-(2-quinolinylmethoxy)-2-naphthalenyl]ethane sulfonamide

A solution of 5.00 g 7-(2-quinolinylmethoxy)-2-naphthalenamine (17 mmol), prepared according to the procedure of Example 7, 1.7 g triethylamine (17 mmol) and 2.18 g ethanesulfonyl chloride (17 mmol) in 50 mL tetrahydrofuran is refluxed overnight. The solvent is removed and the residue is partitioned between methylene chloride and saturated sodium bicarbonate. After drying over potassium carbonate, the organic layer is freed of solvent to afford 5.00 g of a brown gum. Chromatography on alumina and elution with 9:1 methylene chloride/ethyl acetate affords 1.4 g of a white solid which is recrystallized from ethyl acetate. Rechromatography on HPLC and final recrystallization from ethyl acetate affords 0.6 g (9%) of white crystals, m.p. 166°–167.5° C.

Analysis for: $C_{22}H_{20}N_2O_3S$:
Calculated: C, 67.32; H, 5.14; N, 7.14.
Found: C, 67.13; H, 5.18; N, 6.99.

EXAMPLE 9

2-[[(5,6,7,8-tetrahydro-8-methylene-2-naphthalenyl)oxy]methyl]quinoline

To a suspension of 3.6 g (10.1 mmol) of methyltriphenylphosphonium bromide in 50 mL tetrahydrofuran under nitrogen at −50° C. is added n-butyllithium (10 mm as a hexane solution (2.1 M)). After 45 minutes, a solution of 3.0 g (9.90 mmol) of 3,4-dihydro-7-(2-quinolinylmethoxy)-1(2H)-naphthalenone, prepared according to Example 1A above, in 50 mL tetrahydrofuran is added dropwise and the reaction mixture is allowed to slowly come to room temperature. After three days, 50 mL water and 50 mL ether is added. The organic layer is separated, dried over magnesium sulfate and evaporated to 5.0 g of crude product. Chromatography accords 1.3 g (44%) of the desired product. Recrystallization from hexane gives 0.70 g (24%) of white crystals mp 56°–58° C.

Analysis for: $C_{21}H_{19}NO$:
Calculated: C, 83.68; H, 6.35; N, 4.65.
Found: C, 83.51, H, 6.38; N, 4.70.

EXAMPLE 10

N-[7-(2-quinolinyl methoxy)-2-naphthalenyl]trifluoromethane sulfonamide

To a solution of 12.0 (40 mmol) of 7-(2-quinolinyl methoxy)-2-naphthalenamine in 200 mL of methylene chloride at 0° C. containing 6 mL (42 mmol) of triethylamine is added 6.8 mL (40 mmol) of rifluoromethanesulfonic anhydride. The reaction mixture is then allowed to warm to ambient temperature. After stirring overnight, the reaction mixture is washed with water, dried over magnesium sulfate, and evaporated to yield 13.5 g of a brown solid. Trituration with methylene chloride gives 2.7 g of insoluble material which is recrystallized from toluene to afford 1.9 (11%) of white crystals, mp. 172°–175° C.

Analysis for: $C_{21}H_{15}F_3N_2O_3S$:
Calculated: C, 58.33; H, 3.50; N, 6.48.
Found: C, 58.48; H, 3.58; N, 6.14.

EXAMPLE 11

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, J. Roy. Soc. Med., 74, 831 (1981)]. The assay of this Example measures the ability of the compounds of the invention to inhibit the synthesis of 5-HETE by rat glycogen-elicited polymorphonuclear leukocytes.

The array is carried out as follows:

Peritoneal PMN are obtained from female Wistar rats (150–250 g) that received an i.p. injection of 6% glycogen (10 mL). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/mL. To 1 mL portions of cell suspension, test drugs or vehicle are added and incubated at 37° C. for 10 minutes. Following this preincubation, the calcium ionophore (10 $\mu$M), A23187, is added together with 0.5 $\mu$Ci [$^{14}$C] arachidonic acid and further incubated for 10 minutes. The reaction is stopped by the addition of ice cold water (3 mL) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system-hexane:ether:acetic acid (50:50:3). After chromatography, the areas associated with 5-HETE standard are identified by autoradiography, cut out and quantitated by liquid scintillation.

Results are expressed as % inhibition of [$^{14}$C]5-HETE synthesis.

$$\% \text{ inhibition} = \frac{\text{control} - \text{test}}{\text{control}} \times 100$$

Testing compounds of the invention in this assay the following results are obtained, where the concentration of the compounds tested is 50 $\mu$M unless otherwise stated.

TABLE I

| Compound of Example Number | % Inhibition of 5-HETE |
|---|---|
| 1 | >50 |

TABLE I-continued

| Compound of Example Number | % Inhibition of 5-HETE |
| --- | --- |
| 2 | >50 |
| 3 | >50 |
| 4 | >50 |
| 5 | >50 |
| 6 | >50 |
| 7 | >50 |
| 8 | >50 |
| 9 | >50 |

The results show that compounds of this invention have significant activity in inhibiting the synthesis of the arachidonic acid lipoxygenase oxidation product 5-HETE.

EXAMPLE 12

The assay of this Example measures the in vivo ability of the compounds of the invention to inhibit the bronchospasm induced in guinea pigs by the exogenously administered leukotrienes $C_4$ and/or $D_4$. This assay is essentially a measure of the SRS-A antagonist properties of the compounds tested.

This assay is carried out as follows:

Male Hartley strain guinea pigs (350–600g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for $LTC_4$ range from 1 to 2 µg/kg and for $LTD_4$ the range is from 0.3 to 1 µg/kg. The aerosol bronchoprovocation dose for $LTC_4$ is generated from 1.6 µM soution and for $LTD_4$ from a 2.0 µM solution.

Test drugs are administered either intravenously, by aerosol or orally at 1 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 5 minutes are obtained from the recorded charts.

The overflow volume at 5 minutes is expressed as a percentage of maximal bronchoconstriction. Combined group values are used from each of these time intervals to determine the inhibitory effect of drugs.

% inhibition =

% bronchoconstriction (bc) in control group −
%  bc in drug-treated groups
─────────────────────────── × 100
% bc in control group Students t-test for unpaired data is used to determine statistical significance. Dose response curves are generated and $ED_{50}$ doses are interpolated from the regression lines.

Results for a compound of the invention in this assay, using $LTD_4$ for induction of bronchospasm, is given below:

TABLE II

| Compound administered at 10 minutes before induction of bronchospasm | | |
| --- | --- | --- |
| Compound of Example Number | Dose mg/kg (Intraduodenal) | % Inhibition (Statistical Average)* Overflow Volume at 5 min. |
| 1 | 50 | 56.1 |
| 7 | 50 | 88.7 |
| 8 | 50 | 90.6 |
| 10 | 50 | 99.0 |

*average of 6 experiments

The results show that the compounds of the invention tested have significant in vivo activity against $LTD_4$ induced bronchoconstriction.

What is claimed is:

1. A compound having the formula:

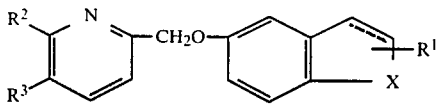

wherein
X is $-CH_2CH_2-$, $-CH=CH-$,

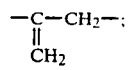

R is hydrogen or loweralkyl;
$R^1$ is hydroxy, amino, loweralkyl sulfonamido, perfluoro loweralkyl sulfonamido or OR;
$R^2$ is hydrogen or loweralkyl;
$R^3$ is hydrogen or loweralkyl; or
$R^2$ and $R^3$ taken together form a benzene ring; and the dotted line represents an optional double bond; and the pharmaceutically acceptable salts thereof.

2. The compound of claim 1, which is 1,2,3,4-tetrahydro-7-(2-quinolinylmethoxy)-1-naphthalenol.

3. The compound of claim 1, which is 7-(2-quinolinylmethoxy)-2-naphthalenol.

4. The compound of claim 1, which is 2-[[(7-methoxy-2-naphthalenyl)oxy]methyl]quinoline.

5. The compound of claim 1, which is 7-(2-pyridinylmethoxy)-2-naphthalenol.

6. The compound of claim 1, which is 7-(2-quinolinylmethoxy)-1-naphthalenamine.

7. The compound of claim 1, which is 7-(2-quinolinylmethoxy)-2-naphthalenamine.

8. The compound of claim 1, which is N-[7-(2-quinolinylmethoxy)-2-naphthalenyl]ethane sulfonamide.

9. The compound of claim 1, which is 2-[[(5,6,7,8-tetrahydro-8-methylene-2-naphthalenyl)oxy]methyl]quinoline.

10. The compound of claim 1, which is N-[7-(2-quinolinyl methoxy)-2-naphthalenyl]trifluoromethane sulfonamide.

* * * * *